US005627157A

United States Patent [19]
Hijiya et al.

[11] Patent Number: 5,627,157
[45] Date of Patent: May 6, 1997

[54] α-GLYCOSYL HESPERIDIN AND ITS USES

[75] Inventors: Hiromi Hijiya; Toshio Miyake, both of Okayama, Japan

[73] Assignee: Kabushiki Kaisha Hayashibara Seibutsu Kagaku Kenkyujo, Okayama, Japan

[21] Appl. No.: 348,146

[22] Filed: Nov. 28, 1994

Related U.S. Application Data

[63] Continuation of Ser. No. 949,376, Sep. 23, 1992, abandoned, which is a continuation of Ser. No. 531,491, May 31, 1990, abandoned.

[30] Foreign Application Priority Data

Jun. 3, 1989 [JP] Japan .................. 1-141902

[51] Int. Cl.$^6$ ...................... A61K 31/70
[52] U.S. Cl. .................. 514/25; 536/8; 514/27; 426/590; 426/658
[58] Field of Search ............ 536/3; 514/25, 514/27; 426/590, 658

[56] References Cited

U.S. PATENT DOCUMENTS 2,700,047  1/1955  Wilson .......................... 536/8
4,521,410  6/1985  Holick et al. .................. 514/26

FOREIGN PATENT DOCUMENTS 0099498  6/1983  Japan .......................... 536/8

OTHER PUBLICATIONS

The Merck Index, ninth edition, Published by Merck & Co., Inc., (1976) pp. 110–111, No. 855.
Rathi et al., Acta Vitaminol. Enzymol. 1983 5(5), 255–261.

*Primary Examiner*—Elli Peselev
*Attorney, Agent, or Firm*—Browdy and Neimark

[57] ABSTRACT

α-Glycosyl hesperidin, a novel hesperidin derivative wherein equimolar or more D-glucose residues are bound to hesperidin via the α-bond, is formed by a saccharide-transferring enzyme in a liquid containing hesperidin and α-glucosyl saccharide. The α-glycosyl hesperidin is easily recovered from the reaction mixture with a synthetic macroporous resin. α-Glycosyl hesperidin is superior in water-solubility, substantially tasteless and odorless, free of toxicity, and readily hydrolyzable in vivo into hesperidin and D-glucose to exhibit the physiological activity inherent to hesperidin. Thus, α-glycosyl hesperidin is favorably usable in vitamin P-enriching agents, foods, beverages, tobaccos, foods, pet foods, pharmaceuticals for susceptive diseases, cosmetics and plastics.

7 Claims, 2 Drawing Sheets

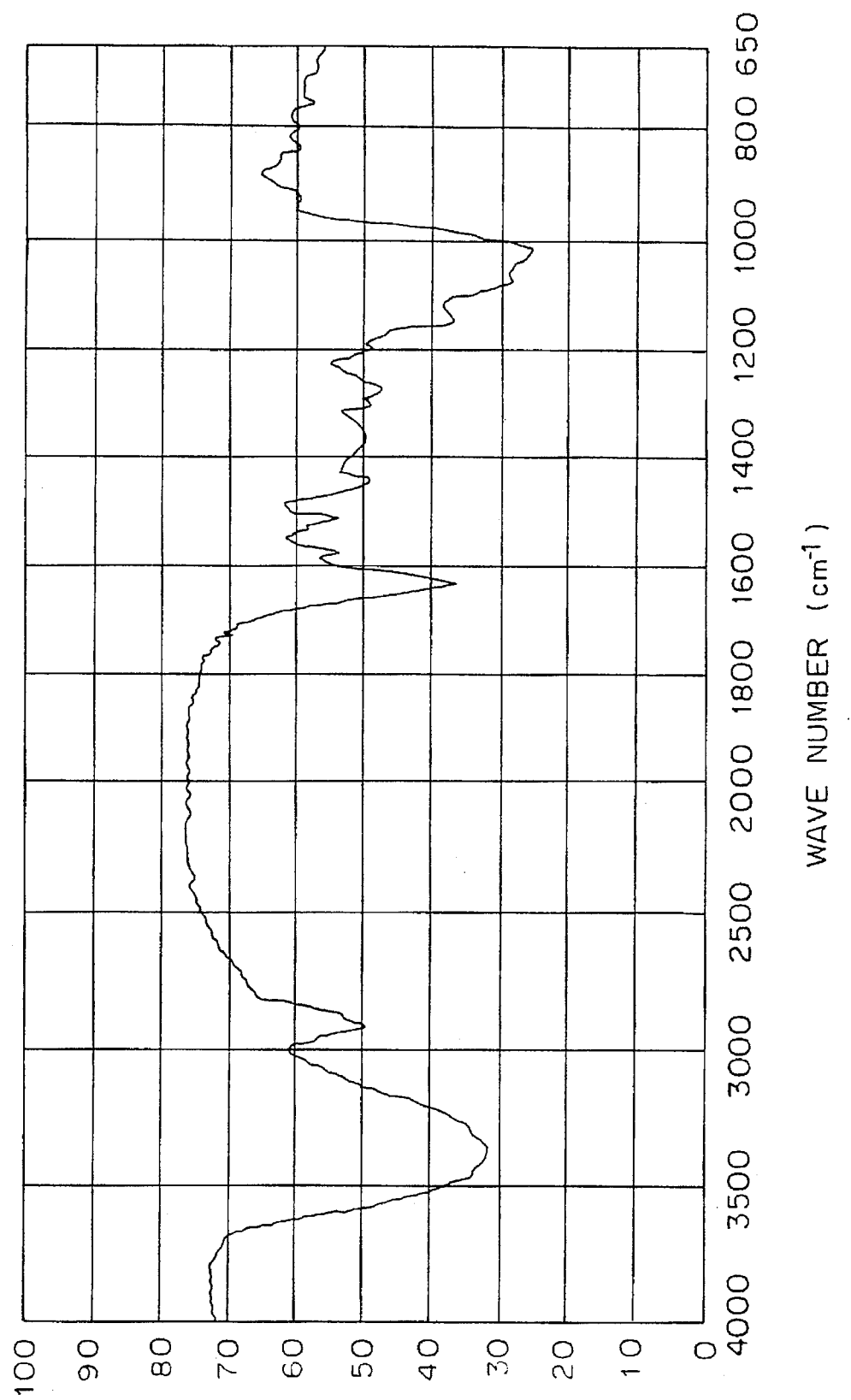

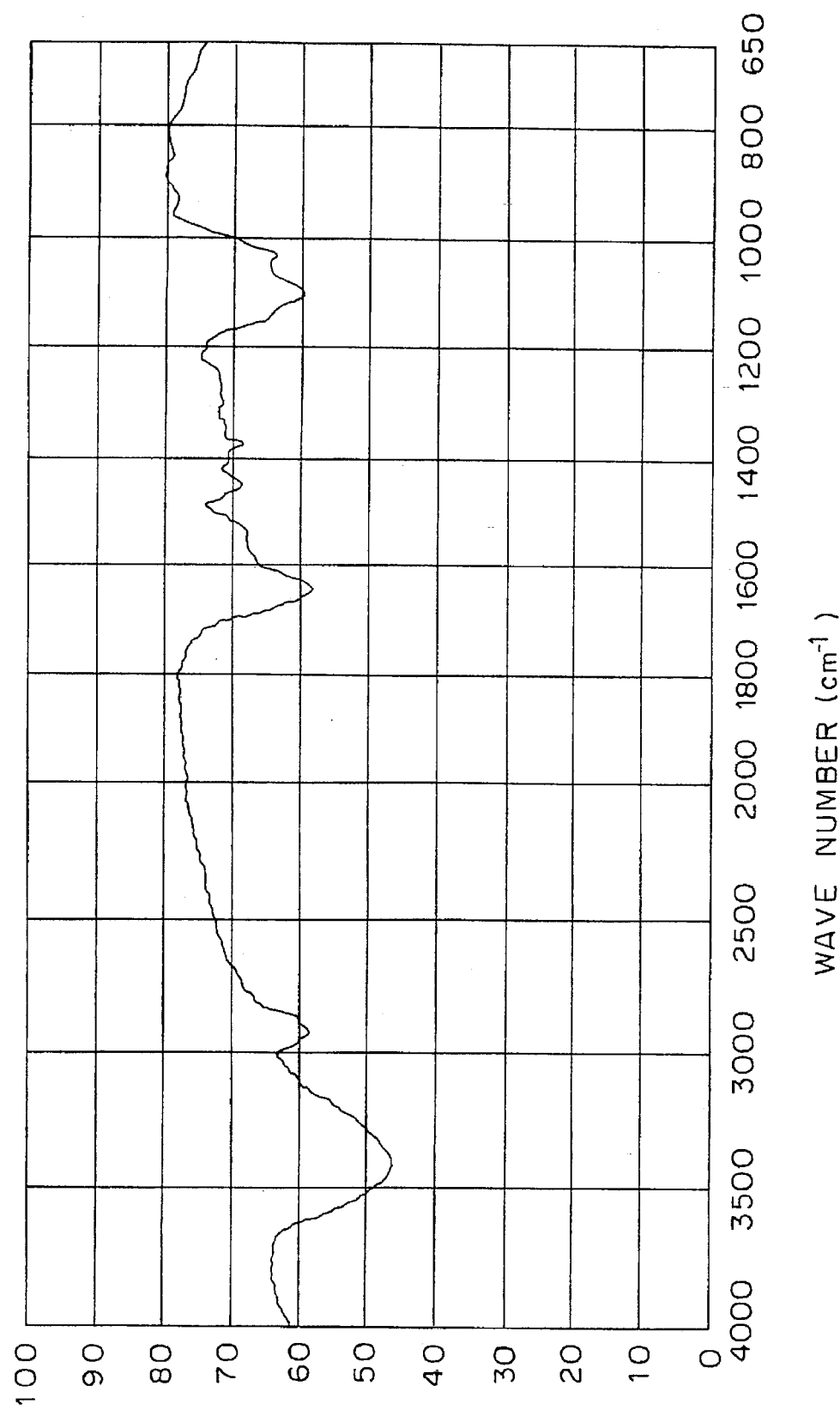

α-GLYCOSYL HESPERIDIN AND ITS USES

This application is a continuation of parent application Ser. No. 07/949,376, filed Sep. 23, 1992, now abandoned, itself a continuation of application Ser. No. 07/531,491, filed May 31, 1990, now abandoned.

BACKGROUND OF THE INVENTION

1. Field of the Invention

The present invention relates to a novel α-glycosyl hesperidin, sometimes hereinafter referred to as α-glucosyl hesperidin, and its preparation and uses.

More particularly, the present invention relates to α-glycosyl hesperidin wherein equimolar or more D-glucose residues are bound to hesperidin via the α-bond.

The present invention also relates to a process to prepare α-glucosyl hesperidin, which comprises allowing a saccharide-transferring enzyme to act on a liquid containing hesperidin together with an α-glucosyl saccharide to form α-glucosyl hesperidin, and recovering the α-glucosyl hesperidin.

The present invention further relates to foodstuffs including beverages and processed foods, pharmaceuticals for susceptive diseases including preventive and remedy therefor, and cosmetics including skin-refining agent-and skin-whitening agent, characterized in that they all contain the α-glucosyl hesperidin obtainable by the process.

2. Description of the Prior Art

Hesperidin, whose chemical structure is given below, has been known as a yellow pigment and vitamin P with physiological activities such as stabilization of blood vessel, prevention of hemorrhage and regulation of blood pressure, and used from ancient times in foodstuffs, pharmaceuticals and cosmetics.

diseases, as well as a yellow coloring agent and uv-absorbent in cosmetics such as skin-refining, melanin-formation inhibitory agent and skin-whitening agents.

Hesperidin is, however, hardly soluble in water (only about 1 g in 50 liters of water or about 0.002 w/v % at ambient temperature). This renders its practical use very difficult.

To improve this low water-solubility, a method wherein dimethyl sulfuric acid is allowed to act on hesperidin to convert it into its methyl derivative having an increased water-solubility has been proposed.

The method is, however, unsatisfactory in view of toxicity, safeness and economical efficiency because it is carried out by an organic chemical procedure using a harmful dimethyl sulfuric acid which renders the purification of the resultant derivative very difficult. Another drawback is that the methyl derivative has a bitter taste.

SUMMARY OF THE INVENTION

Accordingly, the realization of a hesperidin derivative which is free from the drawbacks of conventional hesperidin and its derivatives, in particular, superior in water-solubility, substantially tasteless and odorless, free from toxicity, and exhibits a desired physiological activity in vivo has been in strong demand.

The present invention is to overcome the drawbacks of prior art. We investigated novel hesperidin derivatives by utilizing a biochemical procedure.

As the result, we found that a novel α-glycosyl hesperidin wherein equimolar or more D-glucose residues are bound to hesperidin via the α-bond is formed by allowing a saccharide-transferring enzyme to act on a liquid containing hesperidin together with an α-glucosyl saccharide, as well as that the α-glycosyl hesperidin is superior in water-solubility, substantially tasteless and odorless, free from toxicity, and

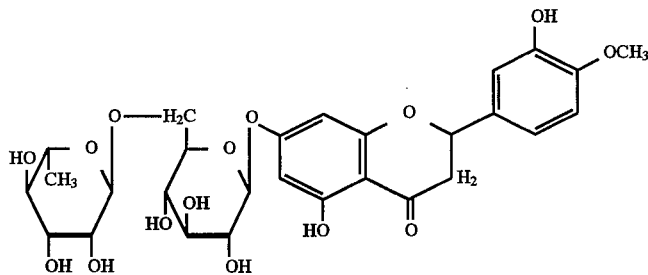

Chemical structure of hesperidin

It is known that vitamin P takes part in some physiological activities of vitamin C in vivo; for example, in the hydroxylation of proline and lysine which are necessary to synthesize collagen as the main element of living connective tissues; the oxidation-reduction reaction of cytochrome C wherein $Fe^{+++}$ is reduced into $Fe^{++}$; and in the immunopotentiation via the increase of leukocyte. These are because vitamin P plays a significant role in the maintenance and promotion of health in living bodies.

Nowadays the use of hesperidin is not limited to agents which enrich vitamin P as a nutritive element, but is extending in various applications. More particularly, because of the chemical structure and physiological activities, hesperidin is useful as a yellow coloring agent and antioxidant alone or in combination with one or more vitamins, for example, in foods, beverages and pharmaceuticals for susceptive diseases such as preventive and remedy for circulatory readily hydrolyzable in vivo to exhibit the physiological activity inherent to hesperidin.

Furthermore, we established its preparation and uses in foodstuffs, pharmaceuticals for susceptive diseases, and cosmetics. Thus, we accomplished the present invention.

We also found that the α-glycosyl hesperidin formed by the saccharide-transfer reaction is easily purified by allowing a reaction mixture to contact with a synthetic macroporous resin, and utilizing the difference in absorbability thereto.

Thus, we confirmed that the process according to the invention completely overcomes the drawback of prior art, and extremely facilitates the commercialization of α-glycosyl hesperidin.

BRIEF EXPLANATION OF THE FIGURES

FIG. 1 shows an infrared absorption spectrum of α-glycosyl hesperidin specimen [I] as an example of the present invention.

FIG. 2 shows an infrared absorption spectrum of α-glycosyl hesperidin specimen [II] as another example of the present invention.

DETAILED DESCRIPTION OF THE INVENTION

The present invention will be explained in detail hereinafter.

The hesperidin usable in the invention shall not be limited to those in a highly-purified form. For example, mixtures with flavonoid glycosides such as citronin, naringin and rutin, and intact and partially-purified extracts from plant tissues are suitable, as long as they contain hesperidin.

Citrus fruits including those in immature form are suitable for the plant tissue, as well as rinds of citrus fruits.

The α-glucosyl saccharides usable in the invention are those which permit a saccharide-transferring enzyme to form α-glycosyl hesperidin from hesperidin. For example, partial starch hydrolysates such as amylose, dextrin, cyclodextrin and maltooligosaccharide, liquefied starch, and gelatinized starch are suitably chosen.

Consequently to facilitate the formation of α-glycosyl hesperidin, it is recommendable to choose for particular saccharide-transferring enzyme an α-glucosyl saccharide having an adequate susceptivity thereto.

For example, in the case of using α-glucosidase (EC 3.2.1.20) as the saccharide-transferring enzyme, maltooligosaccharides such as maltose, maltotriose and maltotetraose are suitable, as well as partial starch hydrolysates having a DE (dextrose equivalent) in the range. of about 10–70. When cyclomaltodextrin glucanotransferase (EC 2.4.1.19) is used as the saccharide-transferring enzyme, gelatinized starches having a DE of below 1 and partial starch hydrolysates having a DE up to about 60 are suitable, as well as cyclodextrins. When α-amylase (EC 3.2.1.1) is used as the saccharide-transferring enzyme, gelatinized starches having a DE of below 1 and dextrins and partial starch hydrolysates having a DE up to about 30 are suitable.

The concentration of such an α-glucosyl saccharide during the reaction is set to a level which is about 0.5–50-fold higher than that of hesperidin.

During the reaction, desirably, hesperidin is kept at the possible highest concentration. For example, such a concentration is feasible with a high-hesperidin content suspension and solution both having a hesperidin content of about 0.005 w/v % or higher, preferably, about 0.01–10.0 w/v %. The latter solution is obtainable by dissolving hesperidin by heating or dissolving hesperidin at an alkaline pH exceeding 7.0.

The saccharide-transferring enzymes usable in the present invention are those which form α-glycosyl hesperidin without decomposing hesperidin when allowed to act on a solution which contains hesperidin together with an α-glucosyl saccharide having an adequate susceptivity to the enzyme.

Examples of such a saccharide-transferring enzyme are α-glucosidases derived from animal and plant tissues such as pig lever and buckwheat seed, and from a culture obtainable by cultivating in a nutrient culture medium microorganisms including molds and yeasts, for example, those of the genera Mucor, Penicillium and Saccharomyces; cyclomaltodextrin glucanotransferases derived from a culture of bacteria such as those of the genera Bacillus and Klebsiella; and α-amylases derived from a culture of bacteria and fungi such as those of the genera Bacillus and Aspergillus.

Such a saccharide-transferring enzyme should not necessarily be purified prior to its use, as long as it fulfills the above requirements. Generally, the present invention is feasible with a crude enzyme.

If necessary, saccharide-transferring enzymes can be purified by conventional method, prior to its use. Of course, commercialized saccharide-transferring enzymes can be used in the invention.

The amount of saccharide-transferring enzyme and reaction time are closely dependent each other. With an economical viewpoint, saccharide-transferring enzyme is used in an amount which completes the reaction within about 5–80 hours.

Immobilized saccharide-transferring enzymes can be suitably used batchwise and in continuous manner.

In the reaction process according to the invention, desirably, the saccharide-transferring enzyme is allowed to act on hesperidin with an increased initial concentration.

For example, in case that hesperidin is allowed to react in suspension, a high-hesperidin content liquid which contains about 0.1–2.0 w/v % hesperidin in suspension together with an appropriate amount of an α-glucosyl saccharide is subjected to a saccharide-transferring enzyme while keeping the liquid at a pH of about 4.5–6.5 and a temperature to the possible highest level where the enzyme is active, in particular, in the range of about 70°–90° C. Thus, as the conversion into α-glycosyl hesperidin proceeds, the hesperidin in suspension gradually dissolves to promptly and readily form α-glycosyl hesperidin at a high concentration.

For example, in case that hesperidin is allowed to react at an alkaline pH exceeding 7.0, a high-hesperidin content liquid which is obtainable by first dissolving about 0.2–5.0 w/v % hesperidin in water at pH 7.5–10.0 by heating, then dissolving in the resultant solution an appropriate amount of an α-glucosyl saccharide is subjected to a saccharide-transferring enzyme while keeping both pH and temperature to the possible highest levels where the enzyme is active, in particular, at a pH in the range of about 7.5–10.0 and a temperature in the range of about 50°–80° C. Thus, α-glycosyl hesperidin is readily formed at a high concentration.

In this case, since hesperidin tends to readily decompose in an alkaline solution, desirably, the liquid is kept under light-shielding and unaerobic conditions in order to prevent such a decomposition.

α-Glycosyl hesperidin can be formed at a high concentration similarly as above by the combination of two or more procedures; for example, by allowing a saccharide-transferring enzyme to act on a high-rutin content liquid which contains an about 0.5–10 w/v % hesperidin together with an appropriate amount of an α-glucosyl saccharide while keeping the liquid at a pH in the range of about 7.5–10.0 and a temperature in the range of 50°–80° C.

Also α-glycosyl hesperidin can be readily formed at a high concentration by dissolving hesperidin in a strongly alkaline aqueous solution, for example, about 0.1–1.0N aqueous solutions of sodium hydroxide, potassium hydroxide, sodium carbonate, calcium hydroxide and ammonia, to give a concentration of about 0.5–10.0 w/v %; adjusting the resultant solution with an aqueous solution of an acid such as hydrochloric acid and sulfuric acid to a pH level where a saccharide-transferring enzyme is active; adding an α-glucosyl saccharide to the solution; and promptly subjecting the solution to the enzyme.

In this case, since the pH adjustment in an aqueous acidic solution tends to cause sedimentation in such a solution wherein hesperidin has been dissolved at a high concentration, desirably, the saccharide-transfer reaction is initiated while suppressing the sedimentation by adding an α-glucosyl saccharide and/or a small amount of α-glycosyl hesperidin, prior to the pH adjustment.

If necessary, in order to increase the solubility of hesperidin to facilitate the saccharide-transfer reaction thereto, one or more water-miscible organic solvents, for example, lower alcohols and ketones such as methanol, ethanol, n-propanol, isopropanol, n-butanol, "ACETOL® (1-hydroxy-2-propanone)" and acetone, can be favorably added to a high-rutin content liquid, prior to the reaction.

The resultant reaction mixture containing α-glycosyl hesperidin may be prepared into final products without no further special treatment. Usually, the reaction mixture is filtered and concentrated into a syrupy product which is, if necessary, dried and prepared into a powdery product.

These products are favorably usable as a highly-safe, natural yellow coloring agent, antioxidant, stabilizer, quality-improving agent, preventive, remedy and uv-absorbent in foods, beverages, tobaccos, feeds, pet foods, pharmaceuticals for susceptive diseases, cosmetics and plastics, as well as a vitamin P-enriching agent.

In case that a purified α-glycosyl hesperidin product is needed, α-glycosyl hesperidin and contaminants including α-glucosyl saccharides are separated by utilizing the difference in adsorbability to a synthetic macroporous resin.

The wording "synthetic macroporous resin" as referred to in the invention means non-ionic, macroporous, synthetic resins which provide a large adsorptive area, such as styrene-divinylbenzen copolymer, phenol-formaldehyde resin, acrylic resin and methacrylate resins. Examples such as such a resin are "Amberlite XAD-1", "Amberlite XAD-2", "Amberlite XAD-4", "Amberlite XAD-7", "Amberlite XAD-8", "Amberlite XAD-11" and "Amberlite XAD-12", products of Rohm & Haas Co., Philadelphia, U.S.A.; "Diaion HP-10", "Diaion HP-20", "Diaion HP-30", "Diaion HP-40" and "Diaion HP-50", products of Mitsubishi Chemical Industries Ltd., Tokyo, Japan; and "Imac Syn-42", "Imac Syn-44" and "Imac Syn-46", products of Industrie de Maatshappily activate N.V., Amsterdam, Netherlands.

The purification process according to the invention contains the step of applying a reaction mixture containing α-glycosyl hesperidin, for example, to a column of a synthetic macroporous resin so that the column adsorbs the α-glycosyl rutin and a relatively small amount of the remaining hesperidin, while large amounts of α-glucosyl and water-soluble saccharides flows out through the column without causing adsorption.

If necessary, after completion of the saccharide-transfer reaction but before treatment with a synthetic macroporous resin, the reaction mixture can be treated by one or more methods; for example, a method wherein the reaction mixture is heated and the insolubilized substances are removed by filtration; another method wherein the reaction mixture is treated, for example, with either magnesium alumino silicate hydrate or magnesium aluminate to adsorb the proteinaceous substances for their removal; and one another method wherein the reaction mixture is deionized with a strongly-acidic ion exchange (H-form) and/or a moderately-alkaline or slightly-alkaline ion exchange (OH-form).

A column of a synthetic macroporous resin on which α-glucosyl hesperidin and a relatively small amount of the remaining hesperidin have been specifically adsorbed are washed with a diluted alkali or water, and then applied with a relatively small amount of an organic solvent or mixture with water, for example, aqueous methanol and aqueous ethanol. Thus, the α-glycosyl hesperidin first elutes, while the intact hesperidin is eluted by continuing the application or increasing the concentration of the organic solvent.

The obtained eluate rich in α-glycosyl hesperidin is distilled to remove the organic solvent, and concentrated to an adequate level. Thus, one can obtain a syrupy product mainly composed of α-glycosyl hesperidin. Subsequent drying and pulverization of the product yield a powdery product mainly composed of α-glycosyl hesperidin.

The elution operation using organic solvents simultaneously regenerates synthetic macroporous resins, and this enables their repeated use.

The purification process using synthetic macroporous resins is characterized in that it can remove, in addition to α-glucosyl and water-soluble saccharides, other contaminants including water-soluble salts.

The α-glycosyl hesperidin thus obtained is characterized by:

(1) It is extremely higher in water-solubility than intact hesperidin.

(2) It is higher in resistance to light and stability than intact hesperidin.

(3) It is hydrolyzable into hesperidin and glucose by the in vivo enzyme system to exhibit the physiological activity inherent to hesperidin, in particular, vitamin P activity. Combination with vitamin C augments the physiological activities of both vitamins.

(4) When an α-glycosyl hesperidin product additionally contains an α-glycosyl saccharide, the α-glycosyl hesperidin exhibits its inherent activities, while the α-glucosyl saccharide exhibits shape-imparting, filling and sweetening activities. A product free from α-glucosyl saccharide is substantially tasteless and odorless, and exhibits the activity of α-glycosyl hesperidin without causing substantial shape-imparting and increase in quantity. Thus, the product is freely usable in seasoning and flavoring.

Because of these, α-glycosyl hesperidin can be favorably incorporated as a yellow coloring agent, antioxidant, stabilizer, quality-improving agent, preventive and remedy for susceptive diseases such as viral diseases, bacterial diseases, circulatory diseases and malignant tumors, and uv-absorbent in foods, beverages, tobaccos, feeds, pet foods, pharmaceuticals for susceptive diseases, cosmetics such as skin-refining agents and skin-whitening agents, and plastics, as well as in agents which are directed to enrich a highly-safe, natural vitamin P.

Since α-glycosyl hesperidin is highly resistant to acid and heat, and well harmonizes with various substances which taste sour, salty, bitter, delicious and astringent, it can be favorably incorporated in foods and beverages in general and tobaccos, for example, seasonings, Japanese-style confectioneries, Western-style confectioneries, ice creams, sherbets, soft drinks, alcoholic drinks, spreads, pastes, pickles, pickled products, bottled products, canned products, meat products, fish meat products, milk products, egg products, processed vegetables, processed fruits and cereals. Furthermore, α-glycosyl hesperidin can be favorably incorporated in feeds and pet foods for domestic animals and poultries including pet animals such as honey bee, silkworm and pet fish in order to enrich them with vitamin P and also to improve their taste qualities.

In addition to the use as a uv-absorbent and deterioration-preventing agent for plastics, α-glycosyl hesperidin can be favorably incorporated in tobaccos, pharmaceuticals including preventive and remedy for susceptive diseases, and cosmetics including skin-refining agent and skin-whitening agent in solid, paste or liquid; for example, cigar, cigarette, troche, cod-liver oil drop, vitamin compound, oral refreshing agent, cachou, gargle, intubation nutrient, internal medicine, injection, dentifrice, lipstick, lip cream and sunscreening.

The wording "susceptive diseases" as referred to in the invention means those which can be prevented and/or treated with α-glucosyl hesperidin, i.e. diseases which are conventionally known to be prevented and/or treated with hesperidin.

The shape and form of pharmaceuticals for susceptive diseases can be freely chosen to meet to their final use; for example, liquid pharmaceuticals such as nebula, collyrium, collunarium, collutory and injection, paste pharmaceuticals such as ointment, cataplasm and cream, and solid pharmaceuticals such as powder, granule, capsule and tablet. In the preparation of such a pharmaceutical, one or more ingredients, for example, remedy, biologically-active substance, antibiotic, adjuvant, filler, stabilizer, coloring agent and flavoring agent, can be suitably used in combination, if necessary.

The dose is adequately changed dependent on the α-glycosyl hesperidin content, administration route and administration frequency; usually, in the range of about 0.001–10.0 g/day/adult as α-glycosyl hesperidin.

Cosmetics can be prepared similarly as in pharmaceuticals.

In use, α-glycosyl hesperidin is incorporated in products by conventional method, for example, mixing, kneading, dissolving, soaking, permeating, spreading, applying, spraying and injecting, before completion of their processing.

The following experiments will illustrate α-glycosyl hesperidin according to the invention.

Experiment 1
Preparation of α-glycosyl hesperidin
Experiment 1(1)
Saccharide-transfer reaction One part by weight of hesperidin and 6 parts by weight of dextrin (DE 20) were added with 5,000 parts by weight of water, and the mixture was dissolved by heating, added with 20 units/g dextrin of cyclomaltodextrin glucanotransferase from *Bacillus stearothermophilus* commercialized by Hayashibara Biochemical Laboratories, Inc., Okayama, Japan, allowed to react for 18 hours while keeping the mixture at pH 6.0 and 70° C., and heated to inactivate the enzyme. Thus, an α-glycosyl hesperidin-containing liquid was obtained.

Experiment 1(2)
Purification

A reaction mixture obtained by the method in Experiment 1(1) was filtered, and the filtrate was applied to a column of "HP-10", a synthetic macroporous resin commercialized by Mitsubishi Chemical Industries Ltd., Tokyo, Japan, at a flow rate of SV 2. The column was then washed with water, and applied with 50 v/v % aqueous ethanol, after which the eluate was concentrated in vacuo to remove the ethanol, and pulverized to obtain a pale yellow α-glycosyl hesperidin specimen [I] in the yield of about 130% against the weight of the starting hesperidin, on the dry solid basis (d.s.b.).

Experiment 1(3)
Hydrolysis by amylase

A small portion of an α-glycosyl hesperidin specimen [I] obtained by the method in Experiment 1(2) was dissolved in water to 1 w/v %, and the solution was added with 100 units/g specimen of glucoamylase (EC 3.2.1.3) commercialized by Seikagaku Kogyo Co., Ltd., Tokyo, Japan, and allowed to react for 5 hours while keeping the solution at pH 5.0 and 55° C. The reaction mixture was heated to inactivate the remaining enzyme and filtered, after which the filtrate was applied to a column of "HP-10", a synthetic macroporous resin commercialized by Mitsubishi Chemical Industries Ltd., Tokyo, Japan, at a flow rate of SV 2. As the result, the column adsorbed the α-glycosyl hesperidin and remaining hesperidin, while such as glucose and salts flew out through the column without causing adsorption. The column was then washed by applying thereto water, and further applied with an aqueous ethanol having a stepwisely increasing concentration to recover an α-glycosyl hesperidin-rich fraction which was then concentrated in vacuo and pulverized to obtain a pale yellow α-glycosyl hesperidin specimen [II] in the yield of about 70% against the weight of the starting hesperidin, d.s.b.

Another portion of the α-glycosyl hesperidin specimen [I] was hydrolyzed similarly as above except that the glucoamylase was replaced with β-amylase (EC 3.2.1.2) commercialized by Seikagaku Kogyo Co., Ltd., Tokyo, Japan, and the resultant hydrolysate was purified, concentrated and pulverized similarly as above to obtain a pale yellow α-glycosyl hesperidin specimen [III] in the yield of about 70% against the weight of the starting hesperidin, d.s.b.

Experiment 2
Characterization of α-glycosyl hesperidin
Experiment 2(1)
Improvement of water-solubility An α-glycosyl hesperidin-containing solution prepared by the method in Experiment 1(1) using the saccharide-transfer reaction, and a control solution which had been prepared similarly except that the enzyme was inactivated by heating prior to its use were allowed to stand at 4° C. for 2 days. As the result, in the control the sedimentation of hesperidin led to a white turbidity, while the solution containing α-glycosyl hesperidin left transparent.

Accordingly, the α-glycosyl hesperidin formed by the saccharide-transfer reaction has an extremely improved water-solubility.

Experiment 2(2)
Solubility in solvents

α-Glycosyl hesperidin specimens were readily soluble in water, 0.1N sodium hydroxide and 0.1N hydrochloric acid; soluble in methanol and ethanol; and hardly soluble in ether benzene and chloroform.

Experiment 2(3)
uv-Absorption spectrum

A small portion of an α-glycosyl hesperidin specimen was dissolved in 0.1N sodium hydroxide solution for the determination of its uv-absorption spectrum. Either of the specimens [I], [II] and [III] exhibited an absorption peak at about 286 nm as intact hesperidin.

Experiment 2(4)
Infrared absorption spectrum

The infrared absorption spectra of α-glycosyl hesperidin specimens were determined by the KBr tablet method. FIGS. 1 and 2 show the infrared absorption spectra of the specimens [I] and [II] respectively.

Experiment 2(5)
Stability against hydrolysis (a) α-Glycosyl hesperidin specimens are hydrolyzable by α-glucosidase (EC 3.2.1.20) derived from pig liver into hesperidin and D-glucose.

(b) Not hydrolyzable by β-glucosidase.

Experiment 2(6)
Thin-layer chromatography
  (a) Analytic procedure Thin-layer plate: "Kieselgel 60 F254" commercialized by Merck & Co., Inc., Rahway, N.J., U.S.A. Developing solvent: n-butanol:acetic acid:water=4:2:1 Color-developing agent: 1 w/w % ceric sulfate in 10 w/w % aqueous sulfuric acid solution
  (b) Results Analysis of the α-glycosyl hesperidin specimens revealed that the specimen [I] exhibited spots at Rf 0.48, 0.34, 0.22, 0.16, 0.10, 0.04 and starting point in addition to a spot at Rf 0.69; the specimen [II], a spot at Rf 0.48; and the specimen [III], spots at Rf 0.48 and 0.34.

The above described physicochemical properties suggest that the substance exhibiting a spot at Rf 0.48 in the specimens [I], [II] and [III] is α-glucosyl hesperidin wherein 1 mole of D-glucose residue is bound to 1 mole hesperidin via the α-bond; the substance exhibiting a spot at Rf 0.34 in the specimens [I] and [III], α-diglucosyl hesperidin wherein 2 moles of D-glucose is bound to 1 mole of hesperidin via the α-bond; and the substance exhibiting a plurality of spots at not higher than Rf 0.22 in the specimen [I], α-oligoglucosyl hesperidin wherein 3 moles or more D-glucose residues are bound to hesperidin via the α-bond.

As described above, the α-glycosyl hesperidin according to the invention wherein equimolar or more D-glucose residues are bound to hesperidin via the α-bond is a novel, satisfactorily-high water-soluble hesperidin derivative which is hydrolyzable by α-glucosidase to exhibit the physiological activity inherent to hesperidin when ingested.

Experiment 3
Acute toxicity

An α-glycosyl hesperidin specimen [I], prepared by the method in Experiment 1(2), was orally administered to 7 week-old dd mice for acute toxicity test. As the result, no mouse died when administered with up to 5 g of the specimen, and higher dose was difficult.

These confirmed that the specimen was extremely low in toxicity. An α-glycosyl hesperidin specimen [II], prepared by the method in Experiment 1(3), was tested similarly as above to obtain the same result, confirming that the toxicity of this specimen was extremely low.

The following Examples A and Examples B will illustrate the preparation and uses of α-glycosyl hesperidin according to the invention.

EXAMPLE A-1

α-Glycosyl hesperidin

One part by weight of hesperidin was dissolved in 4 parts by weight of 1N sodium hydroxide, and the solution was neutralized by the addition of 0.01N hydrochloric acid solution, added with 4 parts by weight of dextrin (DE 10), promptly added with 20 units/g dextrin of cyclomaltodextrin glucano-transferase derived from *Bacillus stearothermophilus* commercialized by Hayashibara Biochemical Laboratories, Inc., Okayama, Japan, and allowed to react for 24 hours under stirring conditions while keeping the solution at pH 6.0 and 75° C. Thin-layer chromatographic analysis of the reaction mixture revealed that about 70% of the hesperidin was converted into α-glycosyl hesperidins such as α-glucosyl hesperidin, α-diglucosyl hesperidin, α-triglucosyl hesperidin, α-tetraglucosyl hesperidin and α-pentaglucosyl hesperidin. Thereafter, the reaction mixture was heated to inactivate the remaining enzyme and filtered, after which the filtrate was deionized and purified with ion exchanges (H- and OH-forms), and concentrated in usual manner to obtain a syrupy α-glycosyl hesperidin product additionally containing α-glucosyl saccharides in the yield of about 90% against the weight of the starting materials, d.s.b.

The product is favorably usable as a highly-safe, natural yellow coloring agent, antioxidant, stabilizer, quality-improving agent, preventive, remedy and uv-absorbent in foods, beverages, tobaccos, feeds, pet foods, pharmaceuticals for susceptive diseases, cosmetics and plastics, as well as in vitamin P-enriching agents.

EXAMPLE A-2

α-Glucosyl hesperidin

One part by weight of a syrupy α-glycosyl hesperidin product additionally containing α-glucosyl saccharides, prepared in accordance with the method in Example A-1 with a slight modification, was dissolved in 4 parts by weight of water, and the solution was added with 100 units/g syrup solid of glucoamylase (EC 3.2.1.3) commercialized by Seikagaku Kogyo, Co., Ltd., Tokyo, Japan, and allowed to react at 50° C. for 5 hours. Thin-layer chromatographic analysis of the reaction mixture revealed that the α-glycosyl hesperidin was converted into α-glucosyl hesperidin.

Thereafter, the reaction mixture was heated to inactivate the remaining enzyme and filtered, after which the filtrate was applied to a column of "HP-10", a macroporous synthetic resin commercialized by Mitsubishi Chemical Industries Ltd., Tokyo, Japan, at a flow rate of SV 2. As the result, the column adsorbed the α-glucosyl hesperidin and remaining hesperidin both present in the reaction mixture, while glucose and salts flew out through the column without causing adsorption. The column was then washed by applying thereto water, and further applied with an aqueous ethanol having a stepwisely increasing concentration to recover an α-glucosyl hesperidin-rich fraction which was then concentrated in vacuo and pulverized to obtain a powdery α-glucosyl hesperidin in the yield of about 60% against the weight of the starting hesperidin, d.s.b.

Acid hydrolysis of the α-glucosyl hesperidin led to the formation of 1 mole of rhamnose and 2 moles of D-glucose per 1 mole hesperidin, while an α-glucosidase, obtained by the extraction from pig liver and partial purification, hydrolyzed α-glucosyl hesperidin into hesperidin and D-glucose.

The product is favorably usable as a yellow coloring agent, antioxidant, stabilizer, quality-improving agent, preventive, remedy and uv-absorbent in foods, beverages, tobaccos, pharmaceuticals for susceptive diseases, and cosmetics, as well as in an agent directed to enrich a highly-purified, readily water-soluble vitamin P.

EXAMPLE A-3

α-Glycosyl hesperidin

One part by weight of hesperidin was dissolved in 500 parts by weight of water at pH 9.5 by heating, and the solution was mixed with another solution which had been separately prepared by dissolving 10 parts by weight of dextrin (DE 8) in 10 parts by weight of water by heating, after which the resultant mixture was added with 30 units/g dextrin of cyclomaltodextrin glucanotransferase, and allowed to react for 40 hours under stirring conditions while keeping the mixture at pH 8.2 and 65° C.

Thin-layer chromatographic analysis of the reaction mixture revealed that about 80% of the hesperidin was converted into α-glycosyl hesperidin.

Thereafter, the reaction mixture was heated to inactivate the remaining enzyme and filtered, after which the filtrate was applied to a column of "XAD-7", a synthetic macroporous resin commercialized by Rohm and Haas Co., Philadelphia, U.S.A., at a flow rate of SV 1.5.

As the result, the column adsorbed the α-glycosyl hesperidin and remaining hesperidin both present in the reaction mixture, while dextrin, oligosaccharides and salts flew out through the column without causing adsorption.

The column was then washed by applying thereto water, and further applied with 50 v/v % aqueous methanol to elute the α-glycosyl hesperidin and hesperidin which were then concentrated and pulverized to obtain a powdery α-glycosyl hesperidin in the yield of about 120% against the weight of the starting hesperidin, d.s.b.

The product is favorably usable as a highly- safe, natural yellow coloring agent, antioxidant, stabilizer, quality-improving agent, preventive, remedy and uv-absorbent in foods, beverages, tobaccos, feeds, pet foods, pharmaceutical for susceptive diseases, cosmetics and plastics, as well as in the use directed to enrich a readily water-soluble vitamin P.

EXAMPLE A-4

α-Glycosyl hesperidin

EXAMPLE A-4 (1)

Preparation of α-glucosidase

Mucor javanicus IFO 4570 was inoculated and cultivated at 30° C. for 44 hours under aeration-agitation conditions in 500 parts by weight of a liquid culture medium which contained water together with 4.0 w/v % maltose, 0.1 w/v % potassium phosphate monobasic, 0.1 w/v % ammonium nitrate, 0.05 w/v % magnesium sulfate, 0.05 w/v % potassium chloride, 0.2 w/v % polypeptone and 1 w/v % calcium carbonate which had been sterilized by heating and sterilely added to the water immediately before the innoculation. After completion of the cultivation, the mycelia was collected from the culture, added with 500 parts by weight of 4M urea in 0.5M acetate buffer (pH 5.3) per 48 parts by weight of the wet mycelia, allowed to stand at 30° C. for 40 hours and centrifuged. The supernatant was dialyzed against flowing water overnight, added with ammonium sulfate to 0.9 saturation, and allowed to stand at 4° C. over-night, after which the resultant sediment was collected, suspended in 50 parts by weight of 0.01M acetate buffer (pH 5.3) and centrifuged. The supernatant was recovered and used as an α-glucosidase specimen.

EXAMPLE A-4(2)

Preparation of α-glycosyl hesperidin

Five parts by weight of hesperidin was dissolved in 100 parts by weight of 0.5N sodium hydroxide solution by heating, and the resultant solution was adjusted to pH 9.5 by the addition of 0.01N hydrochloric acid solution, added with 20 parts by weight of dextrin (DE 30), promptly added with 10 parts by weight of an α-glucosidase prepared by the method in Example A-4(1), and allowed to react for 40 hours under stirring conditions while keeping the solution at pH 8.5 and 55° C.

Thin-layer chromatographic analysis of the reaction mixture revealed that about 60% of the hesperidin was converted into α-glycosyl hesperidin.

Thereafter, the reaction mixture was purified, concentrated and pulverized similarly as in Example A-3 to obtain a powdery α-glycosyl hesperidin product in the yield of about 110% against the weight of the starting hesperidin, d.s.b.

Similarly as the product in Example A-3, the product is feasible as a highly-safe, natural yellow coloring agent, antioxidant, stabilizer, quality-improving agent, preventive, remedy and uv-absorbent, as well as an agent directed to enrich a readily water-soluble vitamin P.

EXAMPLE B-1

Hard candy

Fifteen hundred parts by weight of "MABIT®", a hydrogenated maltose syrup commercialized by Hayashibara Shoji, Inc., Okayama, Japan, was heated, concentrated to a moisture content below about 2%, and mixed to homogeneity with 15 parts by weight of citric acid, 1 part by weight of an α-glycosyl hesperidin powder obtained by the method in Example A-3 and a small amount of lemon flavor, after which the mixture was molded and packaged in usual manner to obtain a hard candy.

The product is a yellow colored, vitamin P-enriched, low-cariogenic and low-caloric lemon candy.

EXAMPLE B-2

"Fuki-no-mizuni (Boiled bog rhubarb )"

Fresh bog rhubargs were pared, cut into short sticks, soaked in a diluted saline, and boiled down in a liquid which contained an α-glycosyl hesperidin syrup obtained by the method in Example A-1 and "Aoiro Ichi-go (Blue No.1)", a green coloring agent, to obtain a freshly green "fuki-no-mizuni)".

The product pleases the eyes when arranged in Japanese traditional cuisines, as well as exhibiting physiological activity as a dietary fiber.

EXAMPLE B-3

"Gyuhi (starch paste)"

One part by weight of waxy rice starch was mixed with 1.2 parts by weight of water, and the mixture was mixed to homogeneity with 1.5 parts by weight of sucrose, 0.7 parts by weight of "SUNMALT®", a crystalline β-maltose commercialized by Hayashibara Co., Ltd., Okayama, Japan, 0.3 parts by weight of starch syrup and 0.2 parts by weight of an α-glycosyl hesperidin syrup obtained by the method in Example A-1 while gelatinizing by heating. Thereafter, the resultant was molded and packaged in usual manner to obtain "gyuhi".

The product is a Japanese-style confectionery with excellent flavor and biting properties, which looks like "kibi-dango (millet dumpling)".

EXAMPLE B-4

Mixed sweetener

A mixed sweetener was obtained by mixing 100 parts by weight of honey, 50 parts by weight of isomerized sugar, 2 parts by weight of "kurozato (unrefined sugar)" and 1 part by weight of an α-glycosyl hesperidin powder obtained by the method in Example A-4.

The product is a vitamin P-enriched sweetener, and suitable for health food.

EXAMPLE B-5

Cream filling

A cream filling was obtained by mixing in usual manner 1,200 parts by weight of "FINETOSE®", a crystalline α-maltose commercialized by Hayashibara Co., Ltd., Okayama, Japan, 1,000 parts by weight of shortening, 10 parts by weight of an α-glycosyl hesperidin powder obtained by the method in Example A-3, 1 part by weight of lecithin, 1 part by weight of lemon oil and 1 part by weight of vanilla oil to homogeneity.

The product is a yellow colored, vitamin P-enriched cream filling which is excellent in taste, flavor, melting and biting properties.

EXAMPLE B-6

Tablet

Twenty parts by weight of ascorbic acid was mixed to homogeneity with 13 parts by weight of crystalline β-maltose, 4 parts by weight of cornstarch and 3 parts by weight of an α-glucosyl hesperidin obtained by the method in Example A-2, and the resultant was tabletted with a 20R punch, diameter of 12 mm.

The product is an easily swallowable vitamin composition containing ascorbic acid and α-glucosyl hesperidin, wherein the ascorbic acid is excellently stable.

EXAMPLE B-7

Capsule

Ten parts by weight of calcium acetate monohydrate, 50 parts by weight of magnesium L-lactate trihydrate, 57 parts by weight of maltose, 20 parts by weight of an α-glucosyl hesperidin obtained by the method in Example A-2, and 12 parts by weight of a γ-cyclodextrin inclusion compound containing 20% eicosapentaenoic acid were mixed to homogeneity, and the mixture was fed to a granulator, and then encapsulated in gelatine to obtain capsules, 150 mg each.

The product is favorably usable as a high-quality blood cholesterol lowering agent, immunopotentiator and skin-refining agent in preventive and remedy for susceptive diseases, as well as in foodstuffs directed to the maintenance and promotion of health.

EXAMPLE B-8

Ointment

One part by weight of sodium acetate trihydrate, 4 parts by weight of DL-calcium lactate and 10 parts by weight of glycerine were mixed to homogeneity, and the mixture was added to another mixture of 50 parts by weight of vaseline, 10 parts by weight of vegetable wax, 10 parts by weight of lanolin, 14.5 parts by weight of sesame oil, 1 part by weight of an α-glycosyl hesperidin obtained by the method in Example A-4 and 0.5 parts by weight of peppermint oil, and mixed to homogeneity to obtain an ointment.

The product is favorably usable as a high-quality sunscreening, skin-refining agent, skin-whitening agent and promoter for healing injury and burn.

EXAMPLE B-9

Injection

An α-glucosyl hesperidin obtained by the method in Example A-2 was dissolved in water, and sterilely filtered in usual manner to obtain a pyrogen-free solution which was then distributed to 20 ml glass vials to give an α-glucosyl hesperidin content of 50 mg, dried in vacuo and sealed to obtain the captioned product.

The product is intramuscularly and intravenously administrable alone or in combination with vitamins and minerals. The product requires no cold storage, and exhibits an excellently high solubility in saline when in use.

EXAMPLE B-10

Injection

Six parts by weight of sodium chloride, 0.3 parts by weight of potassium chloride, 0.2 parts by weight of calcium chloride, 3.1 parts by weight of sodium lactate, 45 parts by weight of maltose and 2 parts of an α-glucosyl hesperidin obtained by the method in Example A-2 were dissolved in 1,000 parts by weight of water, and sterilely filtered in usual manner, after which 250 ml aliquots of the pyrogen-free solution were distributed to sterilized plastic vessels to obtain the captioned product.

The product is capable of supplementing, in addition to vitamin P, calorie and minerals, therefore is favorably usable in the restoration of health during and before suffering from diseases.

EXAMPLE B-11

Intubation nutrient

Twenty four gram aliquots of a compound consisting of 20 parts by weight of crystalline α-maltose, 1.1 parts by weight of glycine, 0.18 parts by weight of sodium glutamate, 1.2 parts by weight of sodium chloride, 1 part by weight of citric acid, 0.4 parts by weight of calcium lactate, 0.1 part by weight of magnesium carbonate, 0.1 part by weight of an α-glycosyl hesperidin obtained by the method in Example A-3, 0.01 part by weight of thyamine and 0.01 part by weight of riboflavin were packed in laminated aluminum bags, and heat-sealed to obtain the captioned product.

In use, one bag of the product is dissolved in about 300–500 ml of water, and the solution is favorably usable as an intubation nutrient directed to oral and parenteral administration to the nasal cavity, stomach and intestine.

EXAMPLE B-12

Bath liquid

A bath liquid was obtained by mixing 21 parts of DL-sodium lactate, 8 parts by weight of sodium pyruvate, 5 parts by weight of an α-glycosyl hesperidin obtained by the method in Example A-1 and 40 parts by weight of ethanol with 26 parts by eight of refined water and appropriate amounts of coloring agent and flavoring agent.

The product is suitable for skin-refining agent and skin-whitening agent, which is diluted by 100–10,000-folds in bath water when in use. In this case, bath water is replaceable with cleansing liquid, astringent and moisture liquid.

EXAMPLE B-13

Milky lotion

One half part by weight of polyoxyethylene behenyl ether, 1 part by weight of polyoxyethylene sorbitol tetraoleate, 1 part by weight of oil-soluble glyceryl monostearate, 0.5 parts by weight of pyruvic acid, 0.5 parts by weight of behenyl alcohol, 1 part by weight of avocado oil, 1 part by weight of an α-glycosyl hesperidin obtained by the method in Example A-3 and appropriate amounts of vitamin E and antiseptic were dissolved by heating in usual manner, and the solution was added with 1 part by weight of L-sodium lactate, 5 parts by weight of 1,3-butylene glycol, 0.1 part by weight of carboxyvinyl polymer and 85.3 parts by weight of refined water, emulsified with a homogenizer, added with an appropriate amount of flavoring agent, and mixed by stirring to obtained the captioned product.

The product is favorably usable as a high-quality sunscreening, skin-refining agent and skin-whitening agent.

EXAMPLE B-14

Cosmetic cream

Two parts by weight of polyoxyethylene glycol monostearate, 5 parts by weight of self-emulsifying glycerine monostearate, 2 parts by weight of an α-glucosyl hesperidin powder obtained by the method in Example A-2, 1 part by weight of liquid paraffin, 10 parts by weight of glyceryl trioctanate and an appropriate amount of antiseptic were dissolved in usual manner by heating, and the mixture was added with 2 parts by weight of L-lactic acid, 5 parts by weight of 1,3-butylene glycol and 66 parts by weight of refined water, emulsified with a homogenizer, added with an appropriate amount of flavoring agent, and mixed by stirring to obtained the captioned product.

The product is favorably usable as a high-quality sunscreen cream, skin-refining agent and skin-whitening agent.

As described above, the α-glycosyl hesperidin of the invention, wherein equimolar or more D-glucose residues are bound to hesperidin via the α-bond, is superior in water-solubility, substantially tasteless and odorless, free of toxicity, and readily hydrolyzable in vivo into hesperidin and D-glucose to exhibits the physiological activity inherent to hesperidin.

The α-glycosyl hesperidin is economically superior and easily commercializable because it is easily produceable by a biochemical procedure wherein a saccharide-transferring enzyme is allowed to act on a liquid containing hesperidin together with an α-glucosyl saccharide.

Furthermore, we found that hesperidin can be allowed to react at an increased initial concentration and this facilitates the formation of α-glycosyl hesperidin at a high concentration. Also was found that in the purification of a reaction mixture, the α-glycosyl hesperidin can be recovered by allowing the reaction mixture to contact with a synthetic macroporous resin. These render the large-scale production of α-glycosyl hesperidin very easy.

Since the α-glycosyl hesperidin thus obtained is characterized in that it exhibits a satisfactorily-high water-solubility, light-resistance, stability and physiological activity, it is favorably usable as a yellow coloring agent, antioxidant, stabilizer, preventive, remedy, uv-absorbent and deterioration-preventing agent in foods, beverages, tobaccos, feeds, pet foods, pharmaceuticals for susceptive diseases, cosmetics including skin-refining agent and skin-whitening agent, and plastics, as well as in a highly-safe, natural vitamin P-enriching agent.

Accordingly, the present invention is extremely significant in food, beverage, cosmetic, pharmaceutical and plastic industries in view of the establishment of industrial-scale production and practical uses for α-glycosyl hesperidin.

We claim:

1. α-Glucosyl hesperidin which is hydrolyzable by α-glucosidase (EC 3.2.1.20) into a mixture consisting of hesperidin and D-glucose residue(s).

2. Food and beverages, which contain an effective amount of an α-glucosyl hesperidin.

3. The foods and beverages of claim 2, which additionally contain vitamin C.

4. In a pharmaceutical composition comprising a pharmaceutically acceptable carrier and hesperidin as an effective ingredient, the improvement comprising said hesperidin being an α-glucosyl hesperidin which is hydrolyzable in vivo by α-glucosidase (EC 3.2.1.20) to exhibit the physiological activities inherent to hesperidin, whereby the water solubility, light resistance and stability of said pharmaceutical composition are improved.

5. The pharmaceutical composition of claim 4, which additionally contains vitamin C.

6. A cosmetic composition which contains as the effective ingredient an effective amount of an α-glucosyl hesperidin.

7. The cosmetic composition of claim 6, which additionally contains vitamin C.

* * * * *